United States Patent [19]
McCombs et al.

[11] Patent Number: 6,065,473
[45] Date of Patent: May 23, 2000

[54] NON-CONTACT GAS DISPENSER AND APPARATUS FOR USE THEREWITH

[75] Inventors: Norman R. McCombs, Tonawanda; Mark R. Mizerkiewicz, N. Tonawanda, both of N.Y.

[73] Assignee: AirSep Corporation, Buffalo, N.Y.

[21] Appl. No.: 09/152,579

[22] Filed: Sep. 14, 1998

Related U.S. Application Data

[63] Continuation-in-part of application No. 08/876,749, Jun. 16, 1997, Pat. No. 5,871,564
[60] Provisional application No. 60/058,806, Sep. 15, 1997, and provisional application No. 60/058,807, Sep. 15, 1997.

[51] Int. Cl.[7] .................................................. A61M 16/00
[52] U.S. Cl. ................ 128/204.18; 128/200.28; 128/200.24; 128/205.26; 128/204.29; 128/207.11
[58] Field of Search ................ 128/204.18, 200.24, 128/205.11, 204.29, 202.26, 204.22, 207.11, 205.26, 200.28; 2/6, 209

[56] References Cited

U.S. PATENT DOCUMENTS

| | | | |
|---|---|---|---|
| 3,433,222 | 3/1969 | Pinto | 128/204.29 |
| 4,377,161 | 3/1983 | Whitt | 128/204.18 |
| 4,428,372 | 1/1984 | Beysel et al. | 128/204.22 |
| 4,593,688 | 6/1986 | Payton | 128/204.18 |
| 4,786,294 | 11/1988 | Jonqueres et al. | 55/28 |
| 5,050,240 | 9/1991 | Sayre | 2/6 |
| 5,138,722 | 8/1992 | Urella et al. | 2/209 |
| 5,642,729 | 7/1997 | Cassidy | 128/204.29 |
| 5,687,713 | 11/1997 | Bahr et al. | 128/204.18 |
| 5,687,715 | 11/1997 | Landis et al. | 128/204.18 |
| 5,690,096 | 11/1997 | Burch | 128/204.18 |
| 5,771,886 | 6/1998 | Maire et al. | 128/207.11 |

*Primary Examiner*—John G. Weiss
*Assistant Examiner*—V. Srivastava
*Attorney, Agent, or Firm*—Jaeckle Fleischmann & Mugel, LLP

[57] ABSTRACT

A non-contact gas dispenser comprising a head set apparatus, a gas source and a conduit for directing the desired gas to a region proximate to the user's nose and mouth. The gas source preferably is a pressure swing adsorption apparatus that allows the user to select one of at least two pre-determined settings of product gas, each setting having a distinct concentration and flow rate different from the other setting(s).

16 Claims, 7 Drawing Sheets

FIG. 10 ns application is a continuation-in-part of application No. 08/876,749, filed Jun. 16, 1997, now U.S. Pat. No. 5,871,564 by Norman R. McCombs for Pressure Swing Adsorption Apparatus, and further claims the priority dates of Provisional Application Ser. No. 60/058,806, filed Sep. 15, 1997, for Non-Contact Gas Dispenser and No. 60/058,807, filed Sep. 15, 1997, for Setting Concentration and Flow Rate in a Pressure Swing Adsorption Apparatus.

NON-CONTACT GAS DISPENSER AND APPARATUS FOR USE THEREWITH

This application is a continuation-in-part of application No. 08/876,749, filed Jun. 16, 1997, now U.S. Pat. No. 5,871,564 by Norman R. McCombs for Pressure Swing Adsorption Apparatus, and further claims the priority dates of Provisional Application Ser. No. 60/058,806, filed Sep. 15, 1997, for Non-Contact Gas Dispenser and No. 60/058,807, filed Sep. 15, 1997, for Setting Concentration and Flow Rate in a Pressure Swing Adsorption Apparatus.

FIELD OF THE INVENTION

This invention relates generally to a non-contact gas dispenser for directing a desired inhalable gaseous mixture to a region proximate to a user's nose and mouth and to a gas concentrator apparatus with which the user may select one of at least two settings to deliver the gaseous mixture at distinct but different concentrations and flow rates.

BACKGROUND OF THE INVENTION

Typically, a desired gas, such as one that is highly concentrated with oxygen generated from a pressure swing adsorption apparatus, or is substantially pure oxygen supplied from a gas canister, is applied to a user by either a mask, a nose or oral cannula, or an oxygen tent. The highly concentrated oxygen gas usually is applied by these means at flow rates up to about 5 liters per minute. Higher flow rates by such applications can irritate the user, and typically will require controlled conditions and/or professional monitoring.

As most uses of such oxygen concentrated gases have been for medical purposes, the conditions for those purposes can be readily controlled. However, there also are non-medical uses which are not monitored or the equipment not pre-set by skilled professionals. Because both efficiency and comfort are needed for those applications, masks and cannulas may not be desirable, and oxygen tents are too confining.

As one example of non-medical uses, oxygen bars have been opening to sell to occasional customers, concentrated oxygen obtained from a pressure swing adsorption apparatus or a gas canister or supply tank. Others may use such oxygen enhancing apparatus during normal exercise routines such as aerobics or weight lifting. Apparently, the consumers believe inhaling concentrated oxygen is beneficial to their well being. That well being, however, may, because of potential injury to air passage tissue, be damaged if non-monitored customers use a highly concentrated oxygen with a mask or nasal cannula. Non-monitored high oxygen concentrations may also lead to oxygen toxicity. With the use of cannulas, significant air passage blockage can occur, with the average inhaled oxygen concentration being different for users with different nostril sizes and intensities of breathing. Exhaled air is less likely to be dissipated when using masks or tents, thus causing exhaled air to be re-inhaled and a change in the humidity of the overall air inhaled. Moreover masks and nasal cannulas are designed to be used once by one person; reuse at oxygen bars or health facilities may cause viruses or other diseases to be transmitted to unsuspecting second users. On the other hand, disposing of a nasal cannula and mask after a one-time use is costly, and environmentally may need to be disposed of as medical waste.

Therefore, we have developed a non-contact gas dispenser that is reusable for various, primarily non-medical users of concentrated oxygen. We also have provided an oxygen concentrator, adapted from known medical-use concentrators for use for these purposes.

SUMMARY OF THE INVENTION

The present invention comprises a non-contact gas dispenser having a head set apparatus, a gas source and a conduit to direct the desired gas from the gas source to the head set and to a region defining the "inspirational area" proximate to the user's nose and mouth. The head set apparatus comprises a gas delivery nozzle and flexible headband with an arm extending from the headband to support the nozzle at a predetermined position within a preferred range near but not in direct contact with the user's mouth, nose or other body tissue.

Moreover, to control the oxygen concentration flow rate within a safe range in non-medically monitored conditions, we provide a pressure swing adsorption apparatus ("PSA") to fractionate air and produce a mixture with a higher but safe concentration of oxygen and having pre-set valve means allowing the user to select among at least two settings for the oxygen enriched gas, each setting having a distinct concentration and flow rate different from the other setting(s).

DETAILED DESCRIPTION OF EMBODIMENTS

Figure 1:
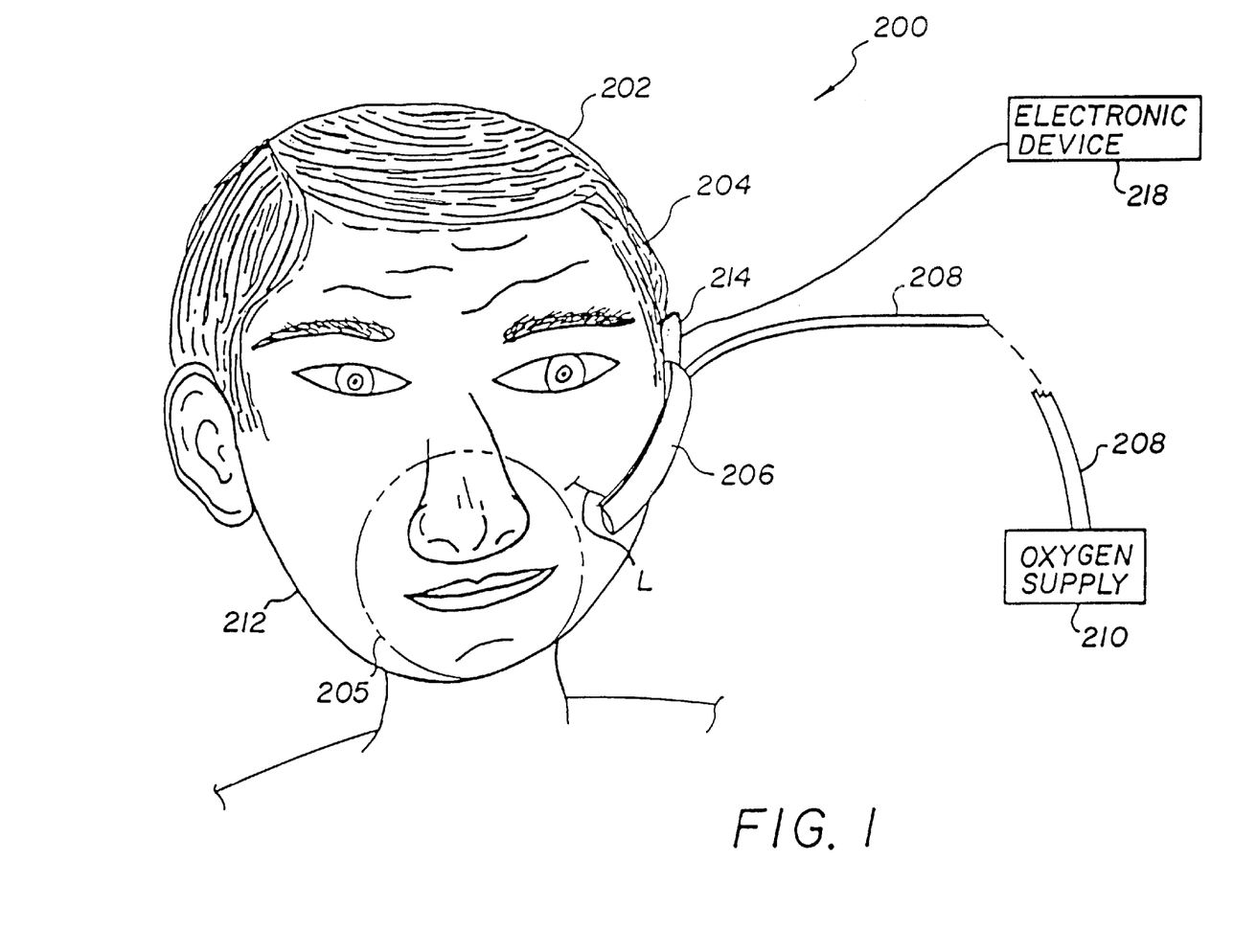
FIG. 1 illustrates a non-contact gas dispenser according to our invention, as may be worn by a user of our invention.
Figure 2:
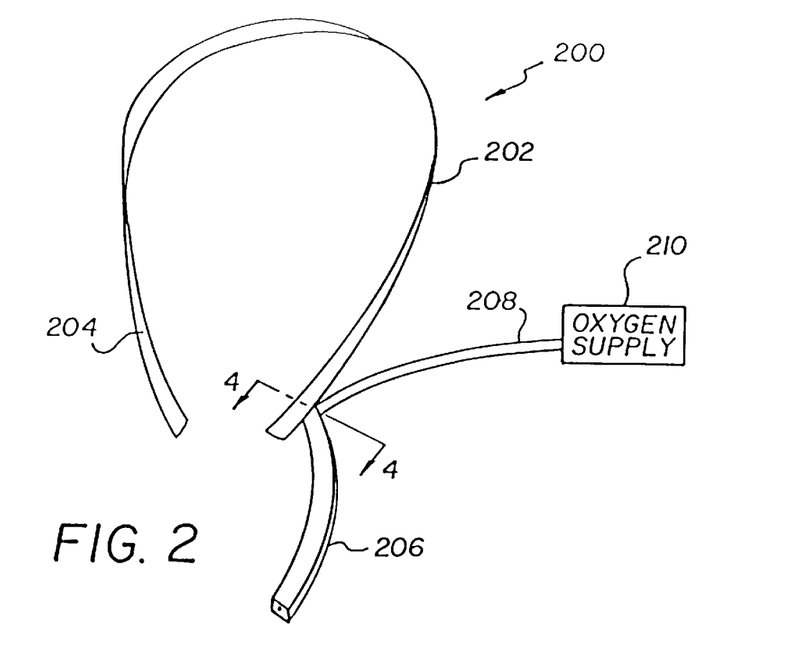
FIG. 2 is a further view of the non-contact gas dispenser of FIG. 1.

Turning now to the drawings and considering first FIG. 1, there is shown an embodiment, generally indicated as 200, of a non-contact gas dispenser in accordance with the present invention. The gas dispenser 200 comprises a head set 202, a gas source 210 producing or storing a desired gas, and a conduit 208 to deliver the desired gas from source 210 to head set 202. Head set 202 comprises an arcuate flexible band 204 extending from one side of a user's head 212 to the other side to support a gas delivery arm 206 to which one end of conduit 208 is attached. Arm 206 extends, as shown, from the band 204 toward the user's mouth and nose to direct the desired gas from conduit 208 to a region proximate to the nose and mouth, defined herein as the inspirational area, shown by dotted lines 205, containing the volume of air from which air is inhaled by nose and mouth.

Figure 3:
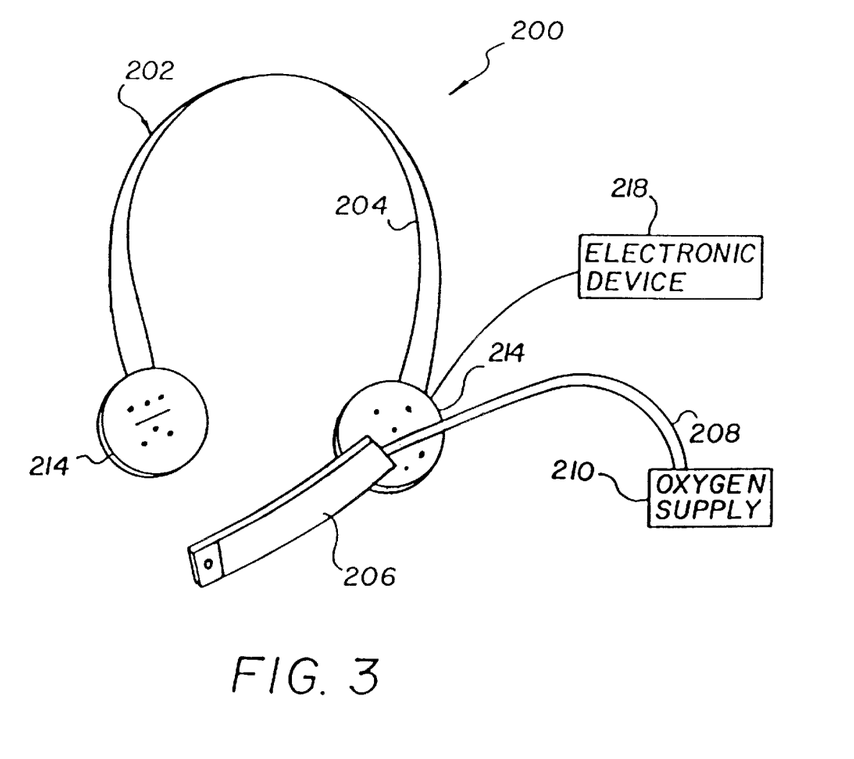
FIG. 3 is an alternative embodiment of a non-contact gas dispenser of our invention.

As is known for making audio head sets, band 204 may be made from any suitable compliant, resilient or elastic material such as a plastic or metal material which may or may not be coated or fabric covered. As shown in FIGS. 1 and 3, band 204 may also, but need not, comprise one or more earphones 214 at its ends. Earphone(s) 214, which can be any type of conventional earphone, foam or liquid/air padded or formed fitted, or replaceable earbuds, may then be connected by known means to an optional sound device 218, such as a radio or other sound source to provide entertainment and/or user instructions timed to the desired gas settings, activities during use, and the use periods. It can thus be seen that a head set according to our invention is useable with many other such devices, including CD players, telephones, televisions, tape cassette recorders and computers.

Turning to FIG. 1, arm 206 is designed not to contact its user during operation. To accomplish this, arm 206 is preset to be a predetermined distance (L) from the user's head 212. At that predetermined distance (L) from the user's head 212, arm 206 can supply the desired gas, in this case an oxygen enriched gas having a preset concentration and flow rate, to the user's inspirational area 205 without nose or throat irritation.

Figure 4A:
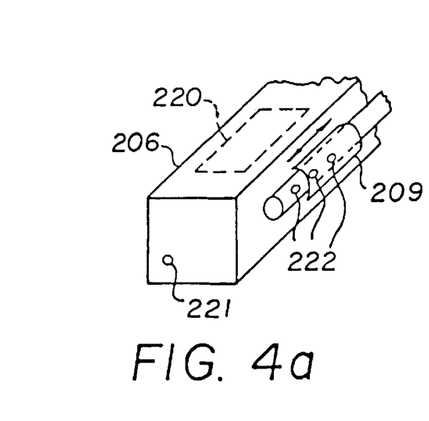
FIGS. 4a through 4g are enlarged views of FIG. 2, taken along lines of 4—4, and illustrating various embodiments for the gas delivery nozzles of the dispenser.
Figure 4B:
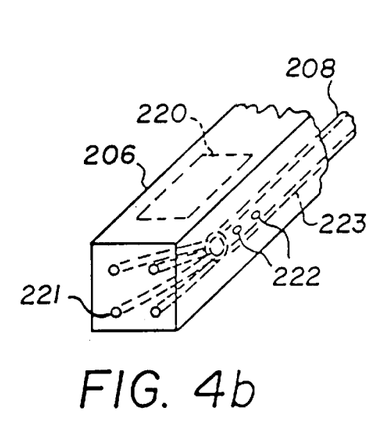
Figure 4C:
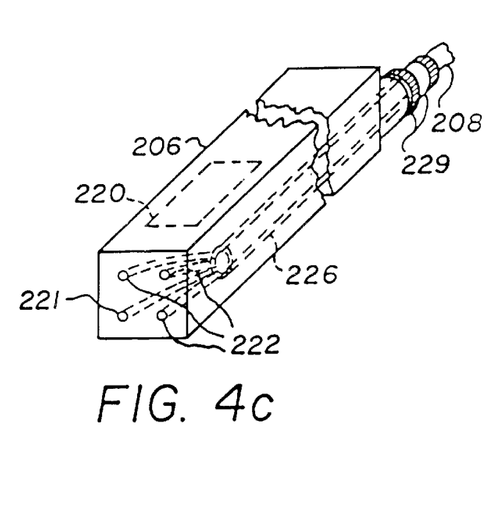
Figure 4D:
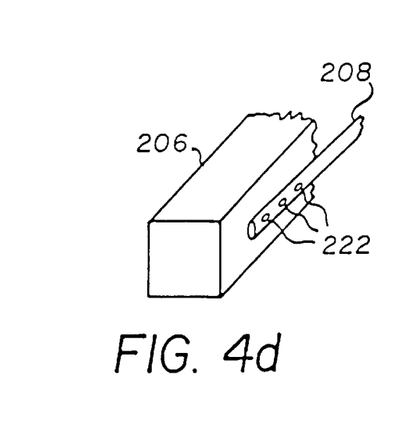
Figure 4E:
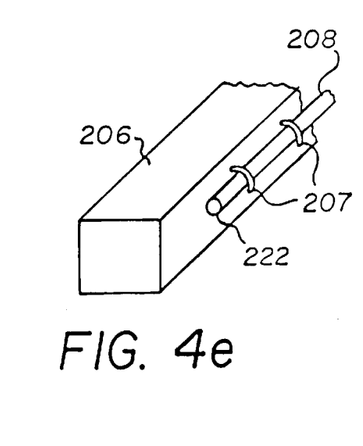

FIGS. 4a through 4g illustrate various embodiments by which the desired gas can be directed to the user's nose and mouth. In FIGS. 4a, 4d and 4e, conduit 208 is attached to the outer surface of arm 206 facing the user's head. The gas is then directed through conduit 208 to the user's nose and mouth through a nozzle 222 comprising either a single aperture at the terminal end of conduit 208, as shown in FIG. 4e, or multiple apertures formed in the wall and/or end of conduit 208, as shown in FIGS. 4a and 4d. In these embodiments, conduit 208 may either be permanently affixed to arm 206 or removeably attached by tube retaining loops 207 or the like as shown in FIG. 4e. Using a nozzle 222 with multiple apertures, the end of conduit 208 may also function as a valve by positioning a slidable cover 209 (shown as dotted lines in FIG. 4a) to vary the number of open apertures through which the gas will pass.

Figure 4F:
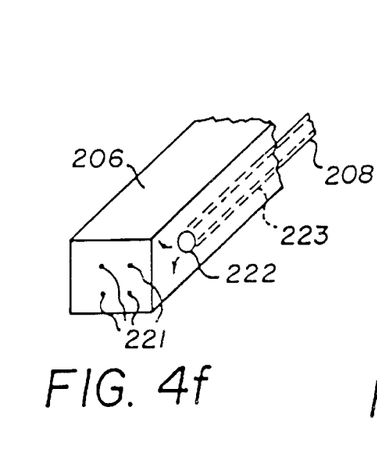
Figure 4G:
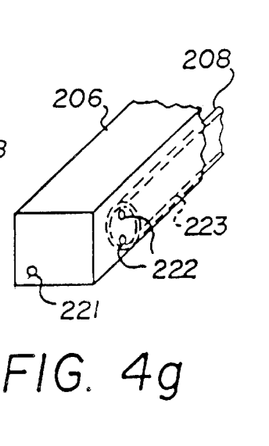

Alternatively, the delivery end of conduit 208 may also be contained within arm 206, as shown in FIGS. 4b and 4f. In these embodiments, the delivery end of conduit 208 is either fixed or detachably held (by a friction fit or the like) in a longitudinally formed hole 223 in arm 206, through which the gas is delivered by nozzle 222 formed by one or more openings in arm 206 in fluid connection with conduit 208 and hole 223.

In yet another embodiment of the present invention, as shown in FIG. 4c, conduit 208 is connected near the non-dispensing end of arm 206 at band 204 by a detachable connector 229 such as a quick release connector or a threaded joint. The desired gas proceeds through conduit 208 into a central passageway 226 in arm 206 until it is directed to the user's nose and mouth through nozzle openings 222, located on the other or gas dispensing end of arm 206.

Conduit 208 can be made of any type suitable material for delivering oxygen, for example, flexible plastic or rubber tubing or articulated hose, that allows the desired gas to be delivered while still permitting the user to move during operation of dispenser 200.

Similarly, arm 206 is manufactured from durable rigid or semi-rigid material, such as plastic or metal. Arm 206 may also contain a voice transmitter 220, as illustrated in FIGS. 4a, 4b and 4c, to be used for a radio, telephone, tape-cassette recorder player, computer or other similar voice activated instruments and medical sensors. A transmitter, schematically shown at 220, receives the user's voice through one of the arm's audio openings 221.

Figure 5A:
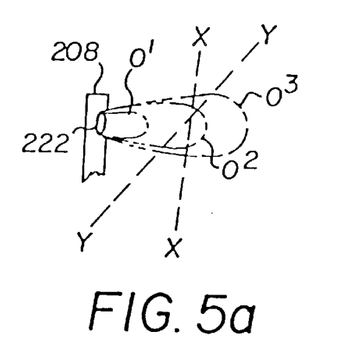
FIGS. 5a and 5b illustrate the distribution of the gaseous mixture in the intended inspirational area for inhalation by the user.
Figure 5B:
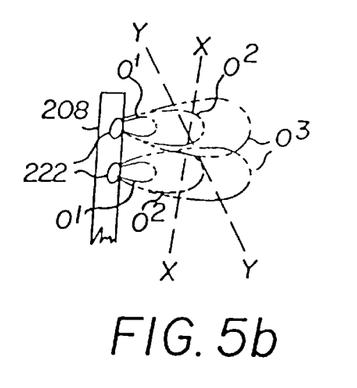

As shown in FIGS. 5a and 5b, there is illustrated the distribution in one plane of a normal gaseous mixture, as it exits a nozzle represented by a single circular opening 222 of, e.g., about ⅛" diameter and flow rate of about 5 liters per minute (FIG. 5a) and of a pair of circular orifices 222 of similar diameter each and flow rate (FIG. 5b). Assuming the gaseous mixture has a ninety percent concentration of oxygen at its source, lines $0^1$, $0^2$ and $0^3$ represent decreasing concentration of oxygens when mixed with the ambient air, of, e.g., 50%, 35% and 25%. In both FIGS. 5a and 5b, line x—x represents the inspirational area 205 of the user if the nozzle is positioned directly in the vertical frontal plane extending outwardly from the nose and mouth, and line y—y if the nozzle is placed to one side, e.g., 45° to the right or left of the vertical plane, but directed toward the center point of the inspirational area 205. The distance of nozzle 222 from the plane of the mouth and nose is shown as L in both FIGS. 5a and 5b.

Figure 6A:
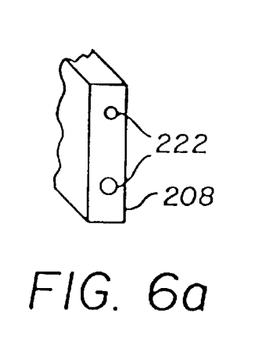
FIG. 6a through 6e illustrate certain possible nozzle combinations and shapes.
Figure 6B:
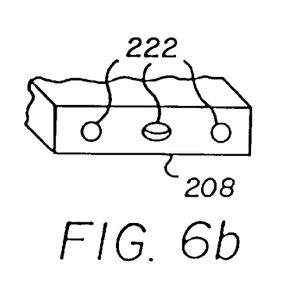
Figure 6C:
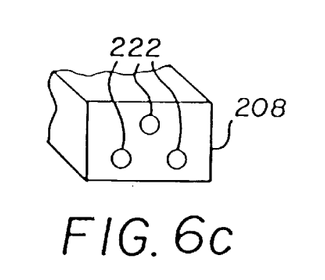
Figure 6D:
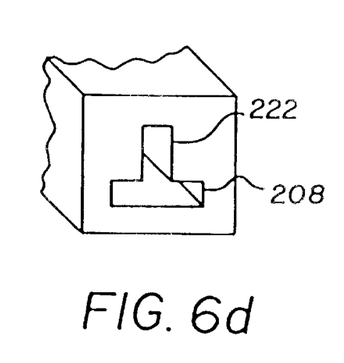
Figure 6E:
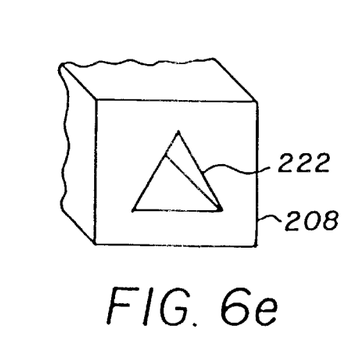

In order to achieve a particular desired distribution pattern for the gaseous mixture, the nozzle openings 222 may be modified, as shown for example in FIGS. 6a through 6e. In FIG. 6a, a pair of nozzle openings 222 may be positioned vertically. If a pear shaped cross-sectional pattern of the gas mixture at the inspiration area 205 is desired, one of the openings 222 may be larger than the other. FIG. 6b illustrates three openings 222 but with the two end openings directing the mixture laterally outwardly and the center opening angled upwardly towards the nose area, whereas FIG. 6c shows the three openings 222 in a triangular pattern. On the other hand, the nozzle may comprise a single opening 222 other than circular in shape, to vary the distribution pattern, as for example the inverse T opening 222 shown in FIG. 6d or the triangular opening 222 in FIG. 6e.

Figure 7A:
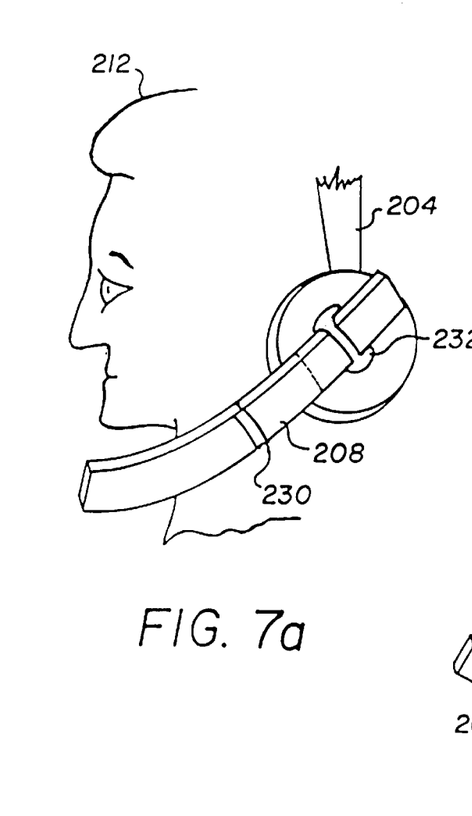
FIGS. 7a through 7c are partial enlarged side views of the head set apparatus showing additional alternative embodiments.
Figure 7B:
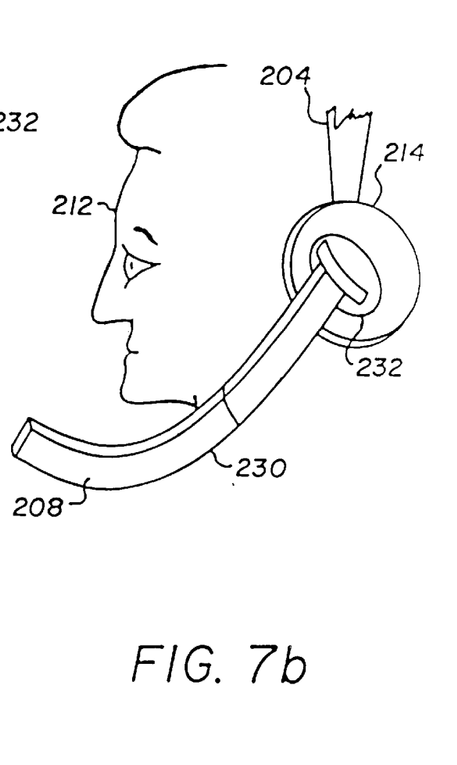
Figure 7C:
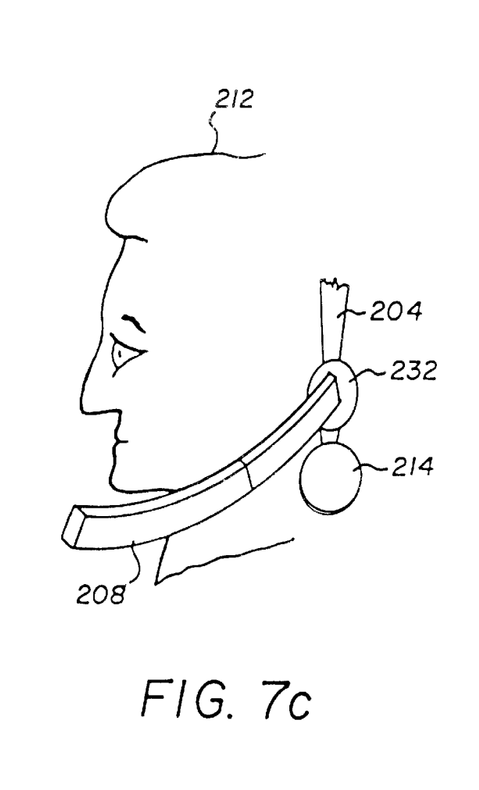

In the alternative embodiments illustrated in FIGS. 7a, 7b and 7c, the distance L between the end of arm 208 and the user's nose and mouth is made adjustable by either the material of arm 208, the structure of arm 208, or both. For example, if arm 208 is made of semi-rigid compliant material, the user may bend the arm to adjust the position of the nozzle end of arm 208. The structure of arm 208 may also include a telescoping portion 230 to adjust the length of arm 208, as shown in its "closed" position in FIG. 7a and in its "opened" position in FIG. 7b. Arm 208 may also be detachably held by retaining means 232, such as a clamp, to earphone 214, as shown in FIGS. 7b and 7c, or to band 204 as shown in FIG. 7a. Retaining means 232 may then hold arm 208 at its pre-set distance L and may also permit limited rotation and sliding within the retaining means to adjust the position of arm 208 within the preferred range to be described.

Figure 8:
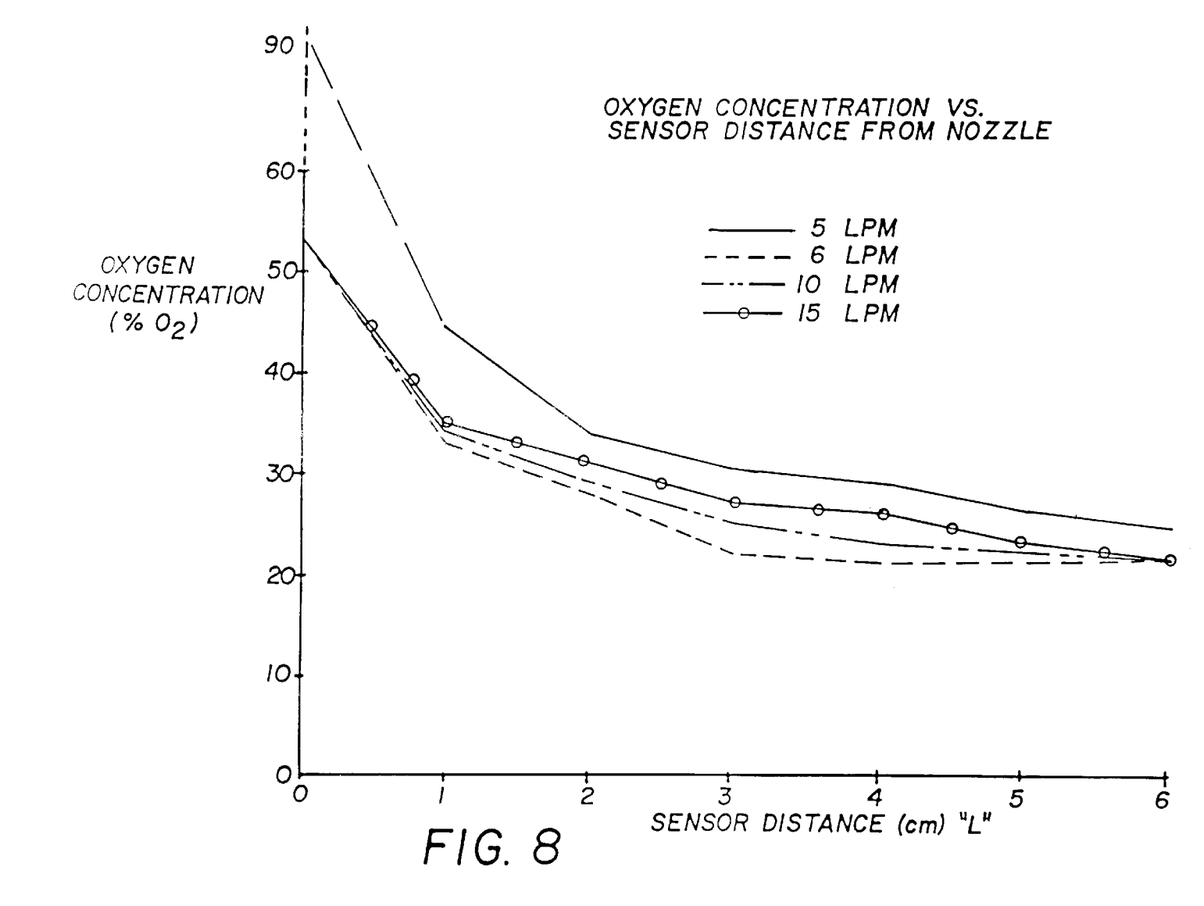
FIG. 8 is a graph illustrating desirable oxygen concentration/nozzle distance parameters according to the invention.

To determine the preferred range for the distance L, a graph such as the one shown in FIG. 8 may be used to plot the concentration of the oxygen mixture as it is diffused from the nozzle end shown as L=O through a distance L, as measured in centimeters, to an asymptotic curve as the mixture dissipates sufficiently to reach atmospheric concentration of about 21% oxygen. If the desired oxygen concentration is about 32%, then it can be seen that the distance L is preferably about 2 cm for a 5 liters per minute (lpm) mixture from a source providing about 90% oxygen. If, on the other hand, a lower concentration of 25% is desired, the oxygen supply is changed to the lower source concentration of 50% to achieve the 25% level without adjusting the nozzle position. Alternatively, the concentration and flow rate can be kept constant, but the nozzle moved to a closed position, as shown in FIG. 7a, of about 5 cm from the inspirational area. We have determined a preferred range for operation of non-contact dispensing apparatus as described to be a range for L from about 2 cm to about 8 cm, with the flow rate ranging from about 3 lpm to about 15 lpm, a pressure of the source from about 7 psig to about 9 psig, and with a source concentration from about 50% oxygen to about 95% oxygen. in order to achieve a preferred range in the inspirational area from about 25% to about 40% oxygen.

Gas source 210 may be any apparatus that provides a desired gas. One such gas source 210 may be a canister or supply tank containing compressed gas, preferably an oxygen enriched gas at a predetermined concentration. Gas source 210 according to our invention may also consist of a pressure swing adsorption apparatus ("PSA") as illustrated in FIG. 6. Such an apparatus is designed for fractionating at least one component or constituent from a gaseous mixture by pressure swing adsorption, such as those disclosed in commonly assigned U.S. Pat. Nos. 4,802,899 and 5,531,807 and U.S. patent application Ser. No. 08/876,749 by Norman R. McCombs (filed Jun. 16, 1997), the entire disclosures of which are incorporated by reference herein.

Figures 9, 10:
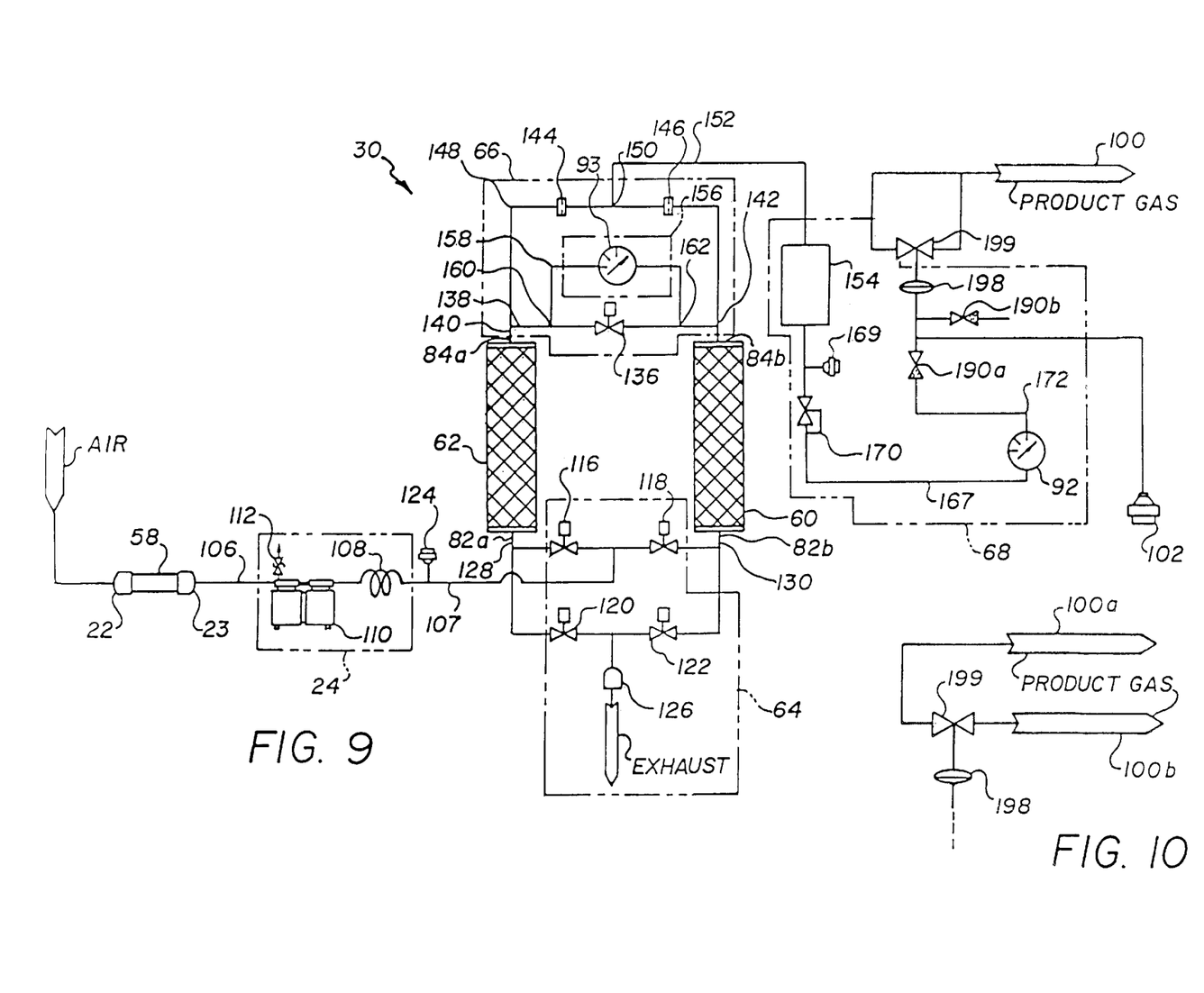
FIG. 9 is a schematic of a pressure swing adsorption apparatus ("PSA") suitable for the present invention.
FIG. 10 illustrates an alternate delivery configuration for the PSA of FIG. 9.

With reference to FIG. 9, and as more fully explained in Ser. No. 08/876,749, ambient air is supplied to source 210 through an assembly of working components 30. The components 30 initially receive a feed gas stream (ambient air) in an input 22 of an intake resonator 58 to decrease the noise for the intake of the ambient air feed stream. The feed stream continues through resonator outlet 23 and is moved through piping 106 and 107, by means of a pump or compressor assembly 24, to a valve block 64, and alternatively to first and second adsorbers 62, 60 through feed valves 116 and 118 and piping 128, 130 respectively.

When the feed stream alternatively enters inlets 82a, 82b of adsorbers 62, 60 in a co-current direction, the respective adsorber fractionates the feed stream into the desired concentration of product gas, which then proceeds through the outlet 84a, 84b of the corresponding adsorber 62, 60 into the product manifold 66.

While in the product manifold 66, the product gas is controllably directed in three directions. The first direction is through T-connection 140 or 142 and piping 138 to a product equalization valve 136. The second direction is through T-connection 140 or 142 and piping 148 to the corresponding purge orifice 144, 146. The third direction is through T-connections 140, 160 or 142, 162 and piping 158 in a second purge loop 156 and through a concentration valve 93. If the applicable purge orifice 144 or 146 is open and concentration valve 93 is closed, the concentration of the product gas will be high. When the applicable purge orifice 144, 146 and concentration valve 93 are both open, the orifice and valve 93 independently control the concentration of the product gas.

As described more fully in the co-pending application, the orifice and valve 93 control the position of a mass transfer zone and water zone of the adsorbers 60, 62 and the concentration range of the product gas. A portion of the product gas proceeds through purge orifices 144, 146, and T-connections 150, 142, and the product gas proceeding through valve 93 and T-connections 162, 142 are counter-currently directed from the outlet 84b, 84a and to the inlet 82b, 80b of the other adsorber 60, 62 to purge adsorbed gases. The counter-current product gas and purged gases then proceed through piping 130 or 128 to valve block 64, in particular waste valve 122 or 120 and waste silencer 126. The balance of the product gas proceeding through the applicable purge orifice 144, 146, which is the usable portion of the produced gas, is directed through T-connection 150 to flow control assembly 68.

Within the flow control assembly 68 are a mixing tank 154, a test block component 169, a pressure regulator 170, a conventional flow controller valve 92, check valves 190a, 190b, a conventional bacteria filter 198, and outlet connector 100. Mixing tank 154 receives the product gas through piping 152 and T-connection 150 to average the product gas to the desired concentration. Once through mixing tank 154, the product gas is pushed through piping 167 and monitored by pressure regulator 170 until it reaches the flow controller valve 93. The product gas flow rate is independently controlled by the flow controller valve 92 to proceed through piping 172 and various check valves 190 to outlet connector 100.

When the adsorber 62, 60 through which gas flowing in the co-current direction is saturated, the process is reversed to cause that adsorber to be purged by delivering product gas in the counter current direction and the feed stream delivered to the other adsorber in the co-current direction. The above-process and the ability to control the desired concentration of oxygen and flow rate of the product gas are more fully described in co-pending application Ser. No. 08/876,749.

Each of the above-identified PSA's generates a product gas having concentrations and flow rates that usually are adjusted by a technician resetting at least two or more valves and/or switches. As will be described, the present invention provides a new and improved PSA that allows a non-trained user to change the setting of the product gas between a limited number but at least two product gas settings in which the product gas has distinct concentrations and flow rates that are predetermined for the intended uses.

For this purpose, we have provided a setting valve 199 in the delivery piping 172 at the exit end. Thus, the resulting product gas from check valves 190, which has a predetermined flow rate and concentration, is then directed to setting valve 199, which is designed to allow the user to select one of at least two settings for the product gas. Each setting of product gas has a distinct concentration and flow rate. To attain the desired settings, setting valve 199 may comprise a multiple outlet port valve that has a distinct orifice or orifice size for each setting. The various orifice sizes allow the user to rapidly change the setting of the product gas to a predetermined concentration and flow rate without altering any other valves of the apparatus. Setting valve 199 may be a three-way manual or solenoid operated valve to alter the product gas, for example, from a 5 liter/minute product gas to a 10 liter/minute product gas. The product gas flow rate can range from about 4 liters/minute to about 15 liters/minute.

To maintain stability of the mass transfer zone as described in application 08/876,749, setting valve 199 preferably is linked mechanically or electronically, by conventional means, to concentration valve 93 to simultaneously adjust valve 93 as setting valve 199 is reset. In addition, the valve 199 may be reset by computer controlled function, as for example in coordination with a user exercise routine having differing degrees of user exertion during the routine.

Product gas is then directed from setting valve 199 to the outlet connector 100, which dispenses the product gas at the selected settings to the user through conduit 208. In one embodiment of the present invention, outlet connecter 100 is a single outlet, or as shown in FIG. 10, outlet connector 100 may comprise separate outlets 110*a*, 100*b* for each setting.

Although the present description is described for the production of a desired concentration of oxygen product gas from ambient air, it is apparent that skilled practitioners could use this delivery system and pressure swing adsorption apparatus for other gases as well.

It will be understood that numerous modifications and substitutions may be made to the described embodiments without departing from the spirit of the invention as claimed.

We claim:

1. A non-contact gas dispenser to be worn by a user for inhalation of oxygen through the nose and/or mouth of the user, the dispenser comprising a source of gas which contains oxygen in a concentration from about 50% oxygen to about 95% oxygen;

a nozzle to dispense the gas to a plane defining an inspirational area for inhalation by the user;

conduit means for delivering the gas from the gas source to the nozzle at a selected flow rate within a range from about 3 liters/minute to about 15 liters/minute;

means for supporting the nozzle in at least two positions proximate to but not in contact with the user's nose or mouth, the two positions being in a range from about 2 cm to about 8 cm from a center point of the inspirational area, and means for adjusting the supporting means to locate the nozzle at a position in which the oxygen concentration at the center point is at a selected amount within a range from about 25% to about 40%.

2. The non-contact gas dispenser of claim 1, wherein the means for supporting the nozzle comprises a head set having an arcuate, flexible band extending from one side of the user's head to the other side, and an arm attached at one end to the band and at its other end to the nozzle.

3. The non-contact gas dispenser of claim 2 wherein the arm defines a passageway in fluid connection with the conduit means to deliver the gas to the user through the passageway, and further comprising connector means for detachably connecting the conduit means to the arm.

4. The non-contact gas dispenser of claim 2 wherein the arm comprises means for detachably retaining the nozzle.

5. The non-contact gas dispenser of claim 1 wherein said supporting means further comprises electrical means for receiving and/or transmitting audio and/or electronic signals.

6. The non-contact gas dispenser of claim 1 wherein the source of gas is a pressurized canister containing the gas.

7. The non-contact gas dispenser of claim 1 wherein said source of gas comprises a pressure swing adsorption apparatus having means for fractionating at least one constituent from a gaseous mixture containing oxygen to increase the concentration of the oxygen, means for changing the concentration and flow rate to at least two different settings, each setting having substantially a fixed concentration and a fixed flow rate, the concentrations and flow rates of the settings being different from each other, and means for selecting either one of the two settings to deliver the gas at the fixed concentration and flow rate for that setting.

8. The non-contact gas dispenser of claim 7 wherein the selecting means comprises a valve having at least two orifice sizes.

9. The non-contact gas dispenser of claim 7 wherein said gas is dispensed at a flow rate of about 5 liters per minute for one of said settings and about 10 liters per minute for the other of said settings.

10. The non-contact gas dispenser of claim 1 wherein the nozzle defines an asymmetrical opening to dispense the gas to the inspirational area in an asymmetrical pattern.

11. The non-contact gas dispenser of claim 10 wherein the nozzle opening comprises a triangular cross section.

12. The non-contact gas dispenser of claim 10 wherein the nozzle opening comprises a T-shaped cross section.

13. The non-contact gas dispenser of claim 10 wherein the nozzle opening comprises at least two holes in which one hole is larger in cross section than the other.

14. A method of selecting a desired concentration of oxygen in a gas to be delivered from a gas source containing the oxygen through a non-contact gas dispenser to a user for inhalation of the gas through the nose and/or mouth of the user, the dispenser comprising a nozzle to dispense the gas to an inspirational area for inhalation by the user; and adjustable means for supporting the nozzle at predetermined distances from the inspirational area but not in contact with the user's nose or mouth, the method comprising the steps of selecting a gas source containing oxygen within a range from about 50% oxygen to about 95% oxygen, delivering the gas through the nozzle at a selected flow rate within a range from about 3 lpm to about 15 lpm, moving the nozzle in increments in a direction toward or away from a point comprising the center of the inspirational area, measuring the concentration of oxygen at the point for each increment of movement, selecting the increment at which the oxygen at the point is at the desired concentration within a range from about 25% to about 40%, measuring the distance between the nozzle and the point at the selected increment to establish a determined position for the nozzle to produce the desired concentration, and setting the adjustable means to support the nozzle at the determined position.

15. The method of claim 14 wherein the predetermined distances are in a range from about 2 cm to about 8 cm.

16. The method of claim 14 wherein the oxygen is supplied at a selected pressure within a range from about 7 psig to about 9 psig.

* * * * *